US008070739B2

(12) United States Patent
Zinger et al.

(10) Patent No.: US 8,070,739 B2

(45) Date of Patent: Dec. 6, 2011

(54) LIQUID DRUG TRANSFER DEVICES FOR FAILSAFE CORRECT SNAP FITTING ONTO MEDICINAL VIALS

(75) Inventors: Freddy Zinger, Ra'anana (IL); Igor Denenburg, Beberi (LV); Moshe Gilboa, Kfar Saba (IL)

(73) Assignee: MEDIMOP Medical Projects Ltd., Ra'anana (IL)

( * ) Notice: Subject to any disclaimer, the term of this patent is extended or adjusted under 35 U.S.C. 154(b) by 309 days.

(21) Appl. No.: 12/063,176

(22) PCT Filed: Aug. 8, 2006

(86) PCT No.: PCT/IL2006/000912

§ 371 (c)(1),
(2), (4) Date: Jan. 8, 2009

(87) PCT Pub. No.: WO2007/017868

PCT Pub. Date: Feb. 15, 2007

(65) Prior Publication Data

US 2009/0177177 A1 Jul. 9, 2009

Related U.S. Application Data

(60) Provisional application No. 60/707,183, filed on Aug. 11, 2005.

(51) Int. Cl.
*A61B 19/00* (2006.01)
*A61M 5/32* (2006.01)

(52) U.S. Cl. ....................................... 604/411; 604/414

(58) Field of Classification Search ........... 604/403–416
See application file for complete search history.

(56) References Cited

U.S. PATENT DOCUMENTS

| | | | |
|---|---|---|---|
| 62,333 | A | 2/1867 | Holl |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |
| 2,968,497 | A | 1/1961 | Treleman |
| 3,059,643 | A | 10/1962 | Barton |
| D198,499 | S | 6/1964 | Harautuneian |
| 3,484,849 | A | 12/1969 | Huebner et al. |

(Continued)

FOREIGN PATENT DOCUMENTS

DE 1913926 A1 9/1970

(Continued)

OTHER PUBLICATIONS

Grifols Vial Adapter Product Literature, 2 pages, Jan. 2002.

(Continued)

*Primary Examiner* — Leslie R. Deak
*Assistant Examiner* — Philip R Wiest
(74) *Attorney, Agent, or Firm* — Panitch Schwarze Belisario & Nadel LLP

(57) ABSTRACT

Liquid drug transfer devices including a vial adapter designed for failsafe correct snap fitting on a medicinal vial for ensuring flow communication with the vial's interior. The vial adapters include at least two non-adjacent vial retention flex members for snap fitting over a vial opening for vial retention purposes and at least two non-adjacent vial guidance flex members longer than their counterpart vial retention flex members for guiding a vial adapter with respect to a vial prior to snap fitting the vial adapter thereon.

2 Claims, 5 Drawing Sheets

U.S. PATENT DOCUMENTS 3,618,637 A 11/1971 Santomieri
3,757,981 A 9/1973 Harris, Sr. et al.
3,826,261 A 7/1974 Killinger et al.
3,885,607 A 5/1975 Peltier
3,957,052 A 5/1976 Topham
3,977,555 A 8/1976 Larson
3,993,063 A 11/1976 Larrabee
4,020,839 A 5/1977 Klapp
4,051,852 A 10/1977 Villari
4,109,670 A 8/1978 Slagel
4,187,848 A 2/1980 Taylor
4,210,173 A 7/1980 Choksi et al.
D257,286 S 10/1980 Folkman
4,253,501 A 3/1981 Ogle
4,296,786 A 10/1981 Brignola
4,314,586 A 2/1982 Folkman
D267,199 S 12/1982 Koenig
D271,421 S 11/1983 Fetterman
4,434,823 A 3/1984 Hudspith
4,475,915 A 10/1984 Sloane
4,493,348 A 1/1985 Lemmons
D280,018 S 8/1985 Scott
4,532,969 A 8/1985 Kwaan
4,564,054 A 1/1986 Gustavsson
4,576,211 A 3/1986 Valentini et al.
4,588,396 A 5/1986 Stroebel et al.
4,588,403 A 5/1986 Weiss et al.
D284,603 S 7/1986 Loignon
4,604,093 A 8/1986 Brown et al.
4,607,671 A 8/1986 Aalto et al.
4,614,437 A 9/1986 Buehler
4,638,975 A 1/1987 Iuchi et al.
4,639,019 A 1/1987 Mittleman
4,667,927 A 5/1987 Oscarsson
4,676,530 A 6/1987 Nordgren et al.
4,697,622 A 10/1987 Swift et al.
4,721,133 A 1/1988 Sundblom
4,729,401 A 3/1988 Raines
4,743,229 A 5/1988 Chu
4,743,243 A 5/1988 Vaillancourt
4,758,235 A 7/1988 Tu
4,759,756 A 7/1988 Forman et al.
4,778,447 A 10/1988 Velde et al.
4,787,898 A 11/1988 Raines
4,834,152 A 5/1989 Howson et al.
4,865,592 A 9/1989 Rycroft
4,909,290 A 3/1990 Coccia
4,967,797 A 11/1990 Manska
D314,050 S 1/1991 Sone
4,997,430 A 3/1991 Van der Heiden et al.
5,035,686 A 7/1991 Crittenden et al.
5,041,105 A 8/1991 D'Alo et al.
5,045,066 A 9/1991 Scheuble et al.
5,049,129 A 9/1991 Zdeb et al.
5,053,015 A 10/1991 Gross
5,061,248 A 10/1991 Sacco
5,088,996 A 2/1992 Kopfer et al.
5,096,575 A 3/1992 Cosack
5,104,387 A 4/1992 Pokorney et al.
5,113,904 A 5/1992 Aslanian
5,122,124 A 6/1992 Novacek et al.
5,125,908 A 6/1992 Cohen
5,171,230 A 12/1992 Eland et al.
5,201,705 A 4/1993 Berglund et al.
5,201,717 A 4/1993 Wyatt et al.
5,203,771 A 4/1993 Melker et al.
5,203,775 A 4/1993 Frank et al.
5,211,638 A 5/1993 Dudar et al.
5,232,109 A 8/1993 Tirrell et al.
5,247,972 A 9/1993 Tetreault
5,269,768 A 12/1993 Cheung
5,270,219 A 12/1993 DeCastro et al.
5,279,576 A 1/1994 Loo et al.
5,288,290 A 2/1994 Brody
5,312,377 A 5/1994 Dalton
5,328,474 A 7/1994 Raines
5,334,163 A 8/1994 Sinnett
5,342,346 A 8/1994 Honda et al.
5,344,417 A 9/1994 Wadsworth, Jr.
5,350,372 A 9/1994 Ikeda et al.
5,364,387 A 11/1994 Sweeney
5,374,264 A 12/1994 Wadsworth, Jr.
5,385,547 A 1/1995 Wong et al.
5,397,303 A 3/1995 Sancoff et al.
5,445,630 A 8/1995 Richmond
5,464,123 A 11/1995 Scarrow
5,466,219 A 11/1995 Lynn et al.
5,466,220 A 11/1995 Brenneman
5,478,337 A 12/1995 Okamoto et al.
5,492,147 A 2/1996 Challender et al.
5,505,714 A 4/1996 Dassa et al.
5,509,433 A 4/1996 Paradis
5,520,659 A 5/1996 Hedges
5,526,853 A 6/1996 McPhee et al.
5,531,695 A 7/1996 Swisher
5,566,729 A 10/1996 Grabenkort et al.
5,569,191 A 10/1996 Meyer
5,573,281 A 11/1996 Keller
5,578,015 A 11/1996 Robb
5,583,052 A 12/1996 Portnoff et al.
5,584,819 A 12/1996 Kopfer
5,591,143 A 1/1997 Trombley, III et al.
5,607,439 A 3/1997 Yoon
5,611,576 A 3/1997 Guala
5,616,203 A 4/1997 Stevens
5,636,660 A 6/1997 Pfleiderer et al.
5,641,010 A 6/1997 Maier
5,647,845 A 7/1997 Haber et al.
5,651,776 A 7/1997 Appling et al.
5,653,686 A 8/1997 Coulter et al.
5,674,195 A 10/1997 Truthan
5,718,346 A 2/1998 Weiler
D393,722 S 4/1998 Fangrow, Jr. et al.
5,738,144 A 4/1998 Rogers
5,743,312 A 4/1998 Pfeifer et al.
5,746,733 A 5/1998 Capaccio et al.
5,755,696 A 5/1998 Caizza
5,772,630 A 6/1998 Ljungquist
5,772,652 A 6/1998 Zielinski
RE35,841 E 7/1998 Frank et al.
5,820,621 A 10/1998 Yale et al.
5,827,262 A 10/1998 Neftel et al.
5,832,971 A 11/1998 Yale et al.
5,833,213 A 11/1998 Ryan
5,834,744 A 11/1998 Risman
5,873,872 A 2/1999 Thibault et al.
5,879,337 A 3/1999 Kuracina et al.
5,879,345 A 3/1999 Aneas
5,887,633 A 3/1999 Yale et al.
5,893,397 A 4/1999 Peterson et al.
5,919,182 A 7/1999 Avallone
5,925,029 A 7/1999 Jansen et al.
5,944,700 A 8/1999 Nguyen et al.
5,971,965 A 10/1999 Mayer
5,989,237 A 11/1999 Fowles et al.
6,003,566 A 12/1999 Thibault et al.
6,004,278 A 12/1999 Botich et al.
6,063,068 A 5/2000 Fowles et al.
D427,308 S 6/2000 Zinger
6,080,132 A 6/2000 Cole et al.
6,090,093 A 7/2000 Thibault et al.
6,099,511 A 8/2000 Devos et al.
6,113,583 A 9/2000 Fowles et al.
6,139,534 A 10/2000 Niedospial, Jr. et al.
6,142,446 A 11/2000 Leinsing
6,156,025 A 12/2000 Niedospial, Jr.
6,159,192 A 12/2000 Fowles et al.
6,174,304 B1 1/2001 Weston
6,221,041 B1 4/2001 Russo
6,221,054 B1 4/2001 Martin et al.
6,238,372 B1 5/2001 Zinger et al.
6,245,044 B1 6/2001 Daw et al.
D445,501 S 7/2001 Niedospial, Jr.
6,258,078 B1 7/2001 Thilly
6,280,430 B1 8/2001 Neftel et al.
6,343,629 B1 * 2/2002 Wessman et al. ............. 141/383
6,348,044 B1 2/2002 Coletti et al.

| | | | |
|---|---|---|---|
| 6,358,236 | B1 | 3/2002 | DeFoggi et al. |
| 6,379,340 | B1 | 4/2002 | Zinger et al. |
| 6,408,897 | B1 | 6/2002 | Laurent et al. |
| 6,409,708 | B1 | 6/2002 | Wessman |
| 6,474,375 | B2 | 11/2002 | Spero et al. |
| 6,478,788 | B1 | 11/2002 | Aneas |
| D468,015 | S | 12/2002 | Horppu |
| 6,503,240 | B1 | 1/2003 | Niedospial, Jr. et al. |
| 6,503,244 | B2 | 1/2003 | Hayman |
| 6,524,278 | B1 | 2/2003 | Campbell et al. |
| D472,316 | S | 3/2003 | Douglas et al. |
| 6,530,903 | B2 | 3/2003 | Wang et al. |
| D472,630 | S | 4/2003 | Douglas et al. |
| 6,544,246 | B1 | 4/2003 | Niedospial, Jr. |
| 6,551,299 | B2 | 4/2003 | Miyoshi et al. |
| 6,558,365 | B2 | 5/2003 | Zinger et al. |
| 6,581,593 | B1 | 6/2003 | Rubin et al. |
| D483,487 | S | 12/2003 | Harding et al. |
| D483,869 | S | 12/2003 | Tran et al. |
| 6,656,433 | B2 | 12/2003 | Sasso |
| 6,666,852 | B2 | 12/2003 | Niedospial, Jr. |
| 6,681,810 | B2 | 1/2004 | Weston |
| 6,681,946 | B1 | 1/2004 | Jansen et al. |
| 6,695,829 | B2 | 2/2004 | Hellstrom et al. |
| 6,699,229 | B2 | 3/2004 | Zinger et al. |
| 6,715,520 | B2 | 4/2004 | Andreasson et al. |
| 6,729,370 | B2 | 5/2004 | Norton et al. |
| 6,736,798 | B2 | 5/2004 | Ohkubo et al. |
| 6,745,998 | B2 | 6/2004 | Doyle |
| 6,752,180 | B2 | 6/2004 | Delay |
| D495,416 | S | 8/2004 | Dimeo et al. |
| D496,457 | S | 9/2004 | Prais et al. |
| 6,832,994 | B2 | 12/2004 | Niedospial, Jr. et al. |
| 6,852,103 | B2 | 2/2005 | Fuller et al. |
| 6,875,203 | B1 | 4/2005 | Fowles et al. |
| 6,875,205 | B2 | 4/2005 | Leinsing |
| 6,878,131 | B2 | 4/2005 | Novacek et al. |
| 6,890,328 | B2 | 5/2005 | Fowles et al. |
| 6,901,975 | B2 | 6/2005 | Aramata et al. |
| 6,949,086 | B2 | 9/2005 | Ferguson et al. |
| RE38,996 | E | 2/2006 | Crawford et al. |
| 6,997,917 | B2 | 2/2006 | Niedospial, Jr. et al. |
| 7,024,968 | B2 | 4/2006 | Raudabough et al. |
| 7,074,216 | B2 | 7/2006 | Fowles et al. |
| 7,083,600 | B2 | 8/2006 | Meloul |
| 7,150,735 | B2 | 12/2006 | Hickle |
| 7,192,423 | B2 | 3/2007 | Wong |
| 7,294,122 | B2 | 11/2007 | Kubo et al. |
| D561,348 | S | 2/2008 | Zinger et al. |
| 7,326,194 | B2 | 2/2008 | Zinger et al. |
| 7,350,764 | B2 | 4/2008 | Raybuck |
| 7,354,422 | B2 | 4/2008 | Riesenberger et al. |
| 7,354,427 | B2 | 4/2008 | Fangrow |
| 7,425,209 | B2 | 9/2008 | Fowles et al. |
| 7,435,246 | B2 | 10/2008 | Zihlmann |
| 7,452,348 | B2 | 11/2008 | Hasegawa |
| 7,470,265 | B2 | 12/2008 | Brugger et al. |
| 7,488,297 | B2 | 2/2009 | Flaherty |
| 7,491,197 | B2 | 2/2009 | Jansen et al. |
| 7,523,967 | B2 | 4/2009 | Steppe |
| D595,420 | S | 6/2009 | Suzuki et al. |
| D595,421 | S | 6/2009 | Suzuki et al. |
| 7,540,865 | B2 | 6/2009 | Griffin et al. |
| D595,862 | S | 7/2009 | Suzuki et al. |
| D595,863 | S | 7/2009 | Suzuki et al. |
| 7,611,487 | B2 | 11/2009 | Woehr et al. |
| 7,611,502 | B2 | 11/2009 | Daly |
| 7,632,261 | B2 | 12/2009 | Zinger et al. |
| 7,654,995 | B2 | 2/2010 | Warren et al. |
| 7,695,445 | B2 | 4/2010 | Yuki |
| 7,722,090 | B2 | 5/2010 | Burton et al. |
| D616,984 | S | 6/2010 | Gilboa |
| 7,731,678 | B2 | 6/2010 | Tennican et al. |
| 7,743,799 | B2 | 6/2010 | Mosler et al. |
| 7,758,082 | B2 | 7/2010 | Weigel et al. |
| 7,771,383 | B2 | 8/2010 | Truitt et al. |
| 7,799,009 | B2 | 9/2010 | Niedospial, Jr. et al. |
| 7,803,140 | B2 | 9/2010 | Fangrow, Jr. |
| 7,879,018 | B2 | 2/2011 | Zinger et al. |

| | | | | |
|---|---|---|---|---|
| 2001/0029360 | A1 | 10/2001 | Miyoshi et al. | |
| 2001/0051793 | A1 | 12/2001 | Weston | |
| 2002/0017328 | A1 | 2/2002 | Loo | |
| 2002/0066715 | A1 | 6/2002 | Niedospial | |
| 2002/0087118 | A1 | 7/2002 | Reynolds et al. | |
| 2002/0087141 | A1 | 7/2002 | Zinger et al. | |
| 2002/0087144 | A1 | 7/2002 | Zinger et al. | |
| 2002/0121496 | A1 | 9/2002 | Thiebault et al. | |
| 2002/0123736 | A1 | 9/2002 | Fowles et al. | |
| 2002/0127150 | A1 | 9/2002 | Sasso | |
| 2002/0173752 | A1 | 11/2002 | Polzin | |
| 2003/0036725 | A1 | 2/2003 | Lavi et al. | |
| 2003/0100866 | A1 | 5/2003 | Reynolds | |
| 2003/0120209 | A1 | 6/2003 | Jensen et al. | |
| 2003/0153895 | A1 | 8/2003 | Leinsing | |
| 2003/0195479 | A1 | 10/2003 | Kuracina et al. | |
| 2003/0199846 | A1 | 10/2003 | Fowles et al. | |
| 2003/0199847 | A1 | 10/2003 | Akerlund et al. | |
| 2004/0044327 | A1 | 3/2004 | Hasegawa | |
| 2004/0073189 | A1 | 4/2004 | Wyatt et al. | |
| 2004/0153047 | A1 | 8/2004 | Blank et al. | |
| 2004/0181192 | A1 | 9/2004 | Cuppy | |
| 2004/0199139 | A1 * | 10/2004 | Fowles et al. | 604/414 |
| 2004/0217315 | A1 | 11/2004 | Doyle | |
| 2004/0236305 | A1 | 11/2004 | Jansen et al. | |
| 2005/0124964 | A1 | 6/2005 | Niedospial et al. | |
| 2005/0137566 | A1 | 6/2005 | Fowles et al. | |
| 2005/0148994 | A1 | 7/2005 | Leinsing | |
| 2006/0030832 | A1 | 2/2006 | Niedospial et al. | |
| 2006/0079834 | A1 | 4/2006 | Tennican et al. | |
| 2006/0089603 | A1 | 4/2006 | Truitt et al. | |
| 2006/0106360 | A1 | 5/2006 | Wong | |
| 2006/0135948 | A1 | 6/2006 | Varma | |
| 2006/0253084 | A1 | 11/2006 | Nordgren | |
| 2007/0060904 | A1 | 3/2007 | Vedrine et al. | |
| 2007/0083164 | A1 | 4/2007 | Barrelle et al. | |
| 2007/0088252 | A1 | 4/2007 | Pestotnik et al. | |
| 2007/0088293 | A1 | 4/2007 | Fangrow | |
| 2007/0088313 | A1 | 4/2007 | Zinger et al. | |
| 2007/0106244 | A1 | 5/2007 | Mosler et al. | |
| 2007/0156112 | A1 | 7/2007 | Walsh | |
| 2007/0167904 | A1 | 7/2007 | Zinger et al. | |
| 2007/0191760 | A1 | 8/2007 | Iguchi et al. | |
| 2007/0191764 | A1 | 8/2007 | Zihlmann | |
| 2007/0191767 | A1 | 8/2007 | Hennessy et al. | |
| 2007/0219483 | A1 | 9/2007 | Kitani et al. | |
| 2007/0244461 | A1 | 10/2007 | Fangrow | |
| 2007/0244462 | A1 | 10/2007 | Fangrow | |
| 2007/0244463 | A1 | 10/2007 | Warren et al. | |
| 2007/0255202 | A1 | 11/2007 | Kitani et al. | |
| 2007/0265574 | A1 | 11/2007 | Tennican et al. | |
| 2007/0265581 | A1 | 11/2007 | Funamura et al. | |
| 2007/0270778 | A9 | 11/2007 | Zinger et al. | |
| 2007/0287953 | A1 | 12/2007 | Ziv et al. | |
| 2008/0009789 | A1 | 1/2008 | Zinger et al. | |
| 2008/0172024 | A1 | 7/2008 | Yow | |
| 2008/0249479 | A1 | 10/2008 | Zinger et al. | |
| 2008/0249498 | A1 | 10/2008 | Fangrow | |
| 2008/0312634 | A1 | 12/2008 | Helmerson et al. | |
| 2009/0012492 | A1 | 1/2009 | Zihlmann | |
| 2009/0054834 | A1 | 2/2009 | Zinger et al. | |
| 2009/0082750 | A1 | 3/2009 | Denenburg et al. | |
| 2009/0143758 | A1 | 6/2009 | Okiyama | |
| 2009/0177177 | A1 | 7/2009 | Zinger et al. | |
| 2009/0177178 | A1 | 7/2009 | Pedersen | |
| 2009/0187140 | A1 | 7/2009 | Racz | |
| 2009/0299325 | A1 | 12/2009 | Vedrine et al. | |
| 2009/0326506 | A1 | 12/2009 | Hasegawa et al. | |
| 2010/0010443 | A1 | 1/2010 | Morgan et al. | |
| 2010/0030181 | A1 | 2/2010 | Helle et al. | |
| 2010/0076397 | A1 | 3/2010 | Reed et al. | |
| 2010/0087786 | A1 | 4/2010 | Zinger et al. | |
| 2010/0228220 | A1 | 9/2010 | Zinger et al. | |
| 2010/0312220 | A1 | 12/2010 | Kalitzki | |

FOREIGN PATENT DOCUMENTS

| | | | |
|---|---|---|---|
| DE | 4122476 | A1 | 1/1993 |
| DE | 19504413 | A1 | 8/1996 |
| DE | 202004012714 | U1 | 11/2004 |

| | | | |
|---|---|---|---|
| EP | 0 195 018 | B1 | 8/1985 |
| EP | 0 258 913 | A2 | 7/1987 |
| EP | 0 192 661 | B1 | 1/1990 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0737467 | A1 | 10/1996 |
| EP | 0806597 | A1 | 11/1997 |
| EP | 0 898 951 | A2 | 3/1999 |
| EP | 1008337 | A1 | 6/2000 |
| EP | 1029526 | A1 | 8/2000 |
| EP | 1051988 | A2 | 11/2000 |
| EP | 0 814 866 | B1 | 6/2001 |
| EP | 1 329 210 | A1 | 7/2003 |
| EP | 1 454 609 | A1 | 9/2004 |
| EP | 1 454 650 | A1 | 9/2004 |
| EP | 1498097 | A2 | 1/2005 |
| EP | 1872824 | A1 | 1/2008 |
| FR | 2029242 | A5 | 10/1970 |
| FR | 2869795 | A1 | 11/2005 |
| GB | 1444210 | A | 7/1976 |
| JP | 4329954 | A | 11/1992 |
| JP | 11503627 | T | 3/1999 |
| JP | 2003-102807 | A | 4/2003 |
| WO | 9403373 | A1 | 2/1994 |
| WO | 9507066 | A1 | 3/1995 |
| WO | 9600053 | A1 | 1/1996 |
| WO | 96/29113 | A1 | 9/1996 |
| WO | 9832411 | A1 | 7/1998 |
| WO | 9837854 | A1 | 9/1998 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 01/91693 | A2 | 12/2001 |
| WO | 0209797 | A1 | 2/2002 |
| WO | 03051423 | A2 | 6/2003 |
| WO | 2004041148 | A1 | 5/2004 |
| WO | 2005105014 | A1 | 2/2005 |
| WO | 2007015233 | A1 | 2/2007 |
| WO | 2007105221 | A1 | 9/2007 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |

OTHER PUBLICATIONS

Novel Transfer, Mixing and Drug Delivery Systems, MOP Medimop Medical Projects, Ltd. Catalog, 4 pages, Rev. 4.
Smart Site® Alaris Medical Systems Product Brochure, 4 pages, Issue 1, Oct. 1999.
Smart Site® Needle-Free Systems, Alaris Medical Systems Webpage, 4 pages, Feb. 2006.
Photographs of Alaris Medical Systems SmartSite® device, 5 pages, 2002.
Non-Vented Vial Access Pin with ULTRASITE® Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/Pages/Mixject.aspx.
http://www.westpharma.com/eu/SiteCollectionDocuments/Recon/mixject%20product%20sheet.pfg: MIXJECT product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376.
Int'l Search Report Issued Aug. 25, 2008 in Int'l Application No. PCT/IL2008/000517.
Written Opinion of the ISR Issued in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued Feb. 3, 2011 in Int'l Application No. PCT/IL2010/000777.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.

* cited by examiner

LIQUID DRUG TRANSFER DEVICES FOR FAILSAFE CORRECT SNAP FITTING ONTO MEDICINAL VIALS

CROSS-REFERENCE TO RELATED APPLICATION

This application is a Section 371 of International Application No. PCT/IL2006/000912, filed Aug. 8, 2006, which was published in the English language on Feb. 15, 2007, under International Publication No. WO 2007/017868 A1, which claims the benefit of U.S. Provisional Patent Application No. 60/707,183, filed Aug. 11, 2005, and the disclosures of which are incorporated herein by reference.

FIELD OF THE INVENTION

The invention pertains to liquid drug transfer devices for snap fitting onto medicinal vials.

BACKGROUND OF THE INVENTION

Medimop Medical Projects Ltd., Ra'anana, Israel (www-.medimop.com) supply liquid drug transfer devices for use with medicinal vials containing liquid or powder drug contents and having a vial opening stopped by a typically rubber stopper. Vials are typically available in 13/14 mm and 20 mm standard sizes, and often contain expensive drugs. The liquid drug transfer devices include inter alia vial adapters with single lumen puncturing spikes, vented vial adapters with dual lumen puncturing spikes, fluid control devices illustrated and described in commonly owned PCT International Publication No. WO96/29113, MIX2VIAL® fluid control devices illustrated and described in commonly owned U.S. Pat. No. 6,558,365 to Zinger et al., in-line MIXJECT® fluid control devices illustrated and described in commonly owned PCT International Publication No. WO 2005/105014, and the like. The liquid drug transfer devices are used by both professional users and also home users, for example, young users, visually impaired users, infirm users, and the like, for self-drug administration purposes in the home.

The liquid drug transfer devices include a plastic molded vial adapter with a generally cylindrical skirt for telescopically slidingly receiving a vial opening therein, an integrally formed hollow puncturing spike for puncturing the vial's stopper and having at least one flow aperture towards the puncturing spike's tip for accessing the vial's interior, and at least one access port in flow communication with the puncturing spike. The skirts typically include four or six flex members including at least two non-adjacent vial retention flex members with at least partially circumferentially extending inwardly protruding vial retention ribs for snap fitting over a vial opening for vial retention purposes. The vial retention flex members are designed such that vial adapters cannot be released from a medicinal vial after being snap fitted thereon for sterilization purposes. Flex members not employed for vial retention purposes have smooth inner surfaces for bearing against a vial opening for stabilization purposes. Such vial stabilization flex members are typically of the same length as their counterpart vial retention flex members but maybe shorter, for example, as shown in US Patent Application Publication No. 2003/0199847 to Akerlund et al.

Misalignment of a liquid drug transfer device with respect to a vial results in puncturing difficulties and in some instances its vial adapter's puncturing spike's tip being embedded in the vial's stopper, thereby precluding flow communication with the vial's interior. In such instances, notwithstanding that a vial contains a full dosage of medicament, it is necessarily discarded. It has been long recognized that inaccurate snap fitting of vial adapters on vials can be at least partially contributed to a problematic design feature of medicinal vials described hereinafter. Professional users of liquid drug delivery devices are generally aware of this design feature but are still prone to inaccurately snap fit a vial adapter on a vial due to time pressure, and the like. Home users of liquid drug delivery devices are often not even aware of the design feature and are therefore even more prone to inaccurately snap fit a vial adapter on a vial despite their best efforts.

SUMMARY OF THE INVENTION

The present invention is directed towards liquid drug transfer devices including a vial adapter designed for failsafe correct snap fitting on a medicinal vial for ensuring flow communication with the vial's interior. The vial adapters include at least two non-adjacent vial retention flex members for snap fitting on a vial opening for vial retention purposes and at least two non-adjacent vial guidance flex members longer than their counterpart vial retention flex members for guiding a vial adapter with respect to a vial prior to snap fitting the vial adapter thereon. The vial guidance flex members are designed such that they assist a user to correctly co-axially align a liquid drug delivery device with respect to a vial prior to the former's puncturing spike touches the latter's stopper. Moreover, the vial guidance flex members have the tendency to cause a user to more cautiously approach a snap fitting procedure, thereby considerably assisting in correct snap fittings.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1:
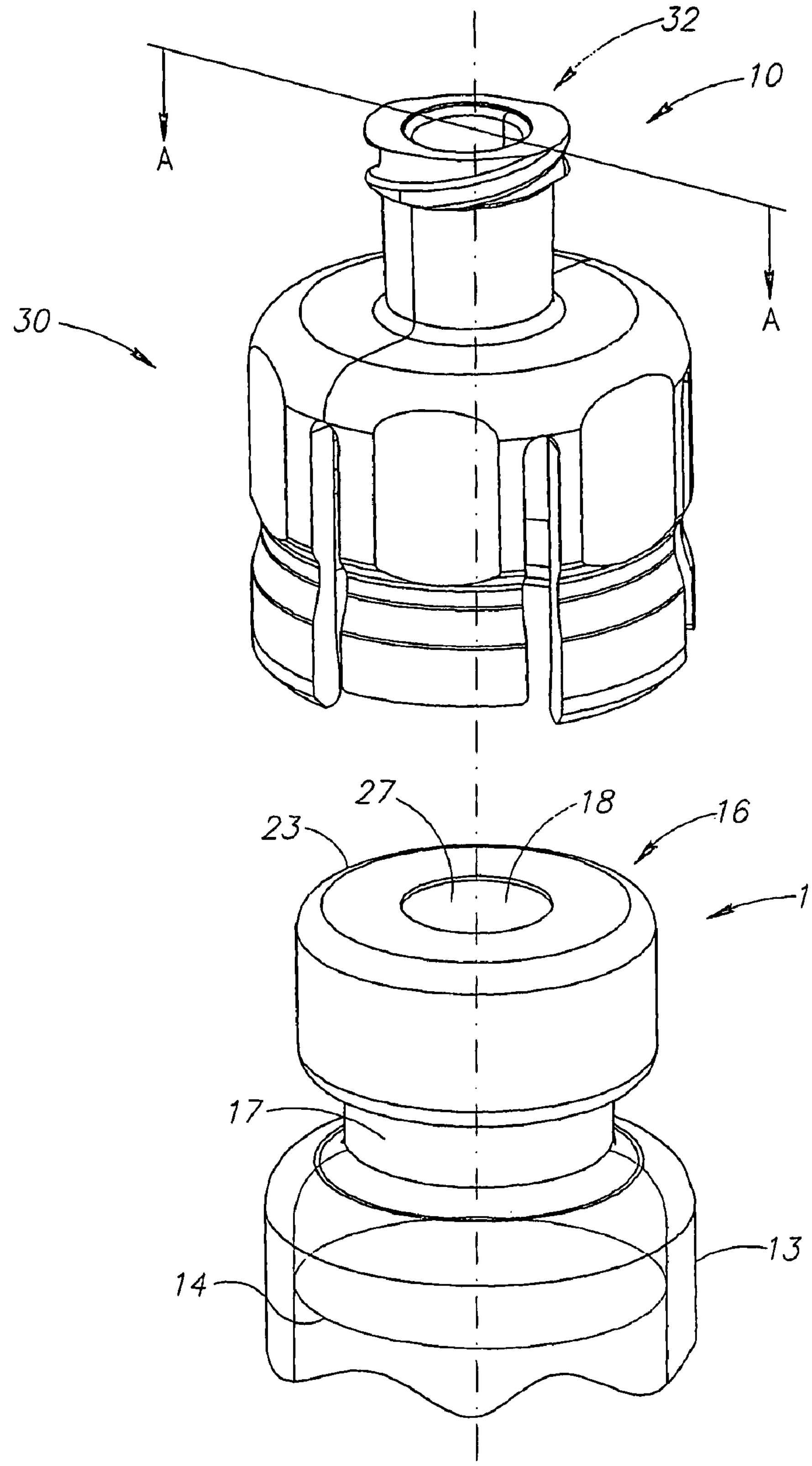
FIG. 1 is a pictorial view of a first preferred embodiment of a liquid drug transfer device with a vial adapter for failsafe correct snap fitting on a medicinal vial.
Figure 2:
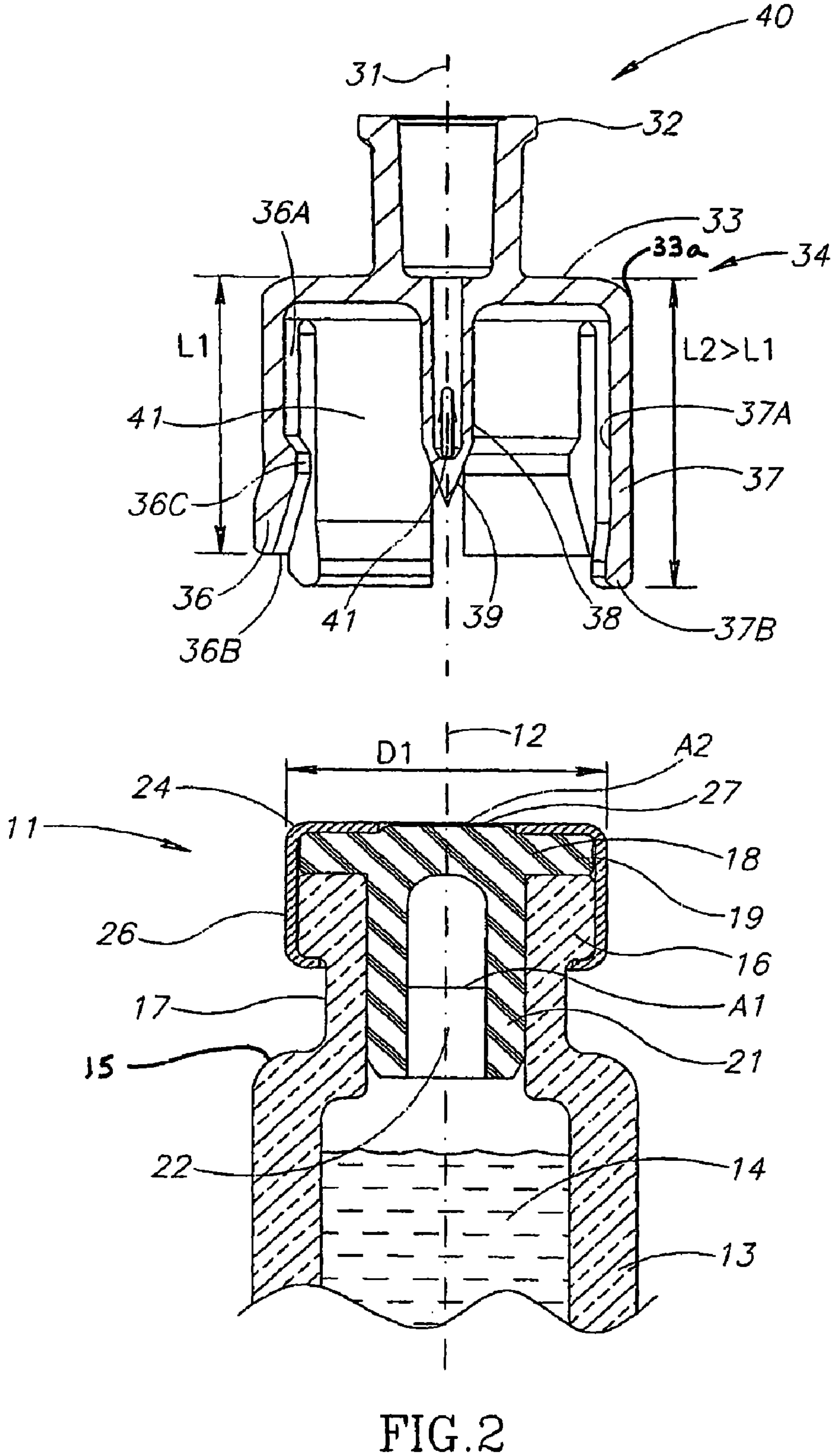
FIG. 2 is a longitudinal cross section of the liquid drug transfer device and the medicinal vial along line A-A in FIG. 1.
Figure 3C:
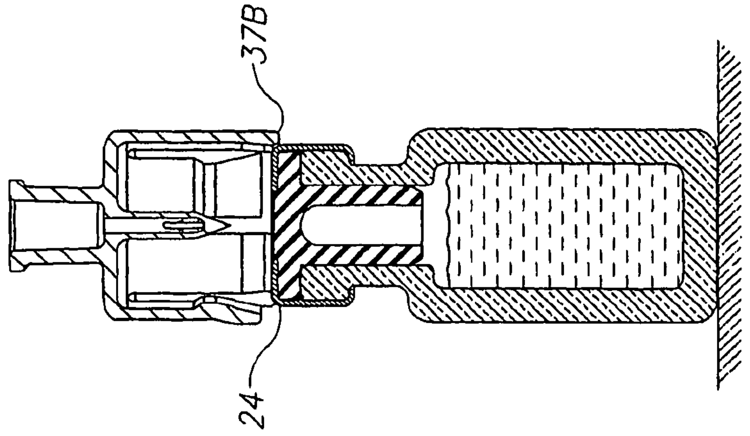
FIG. 3C is a longitudinal cross section of the liquid drug transfer device co-axially aligned with respect to the medicinal vial for failsafe correct snap fitting thereon.
Figure 3B:
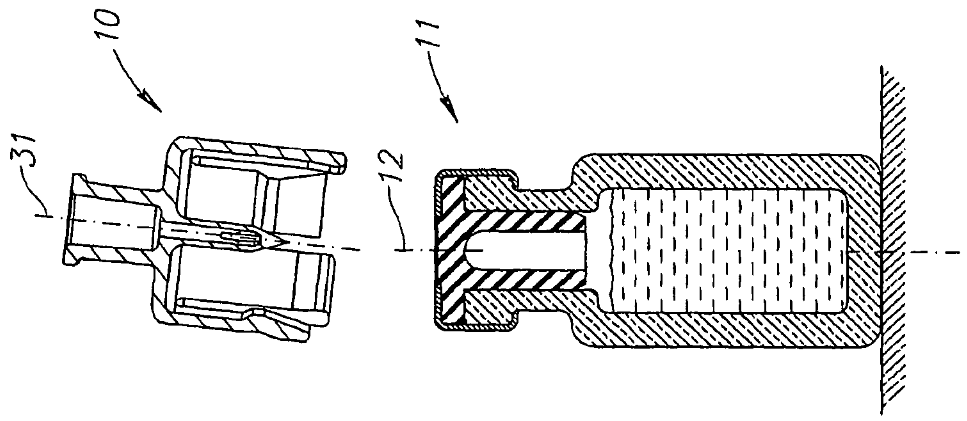
FIG. 3B is a longitudinal cross section demonstrating a liquid drug transfer device angled with respect to the medicinal vial.
Figure 3A:
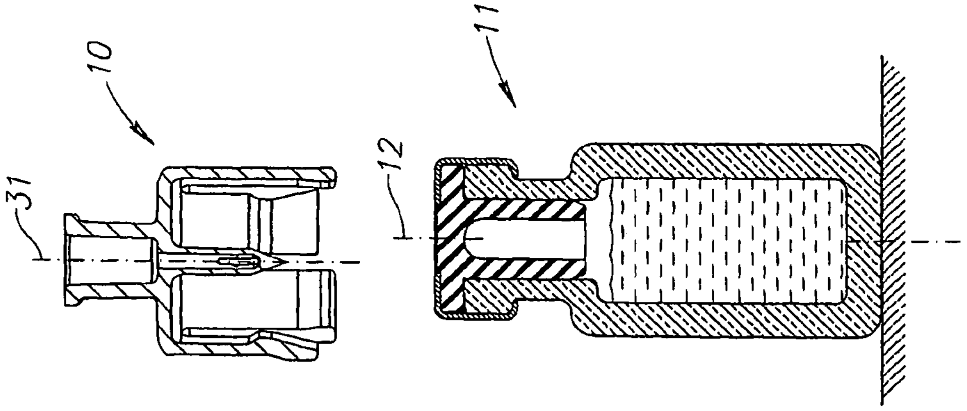
FIG. 3A is a longitudinal cross section demonstrating a liquid drug transfer device off centered with respect to the medicinal vial.
Figure 3E:
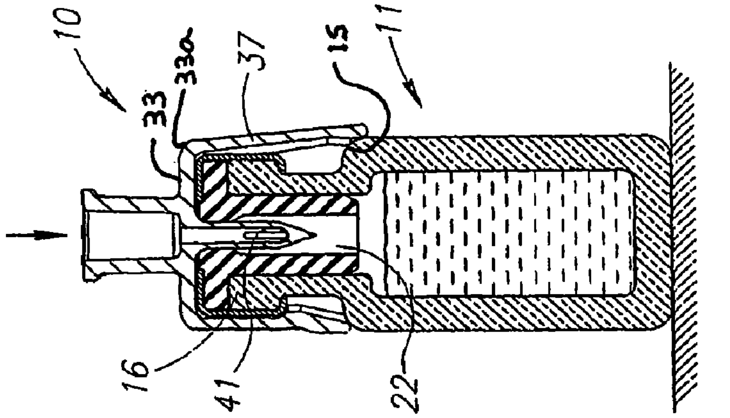
FIG. 3E is a longitudinal cross section of the liquid drug transfer device snap fitted on the medicinal vial and in flow communication with the vial's interior.
Figure 3D:
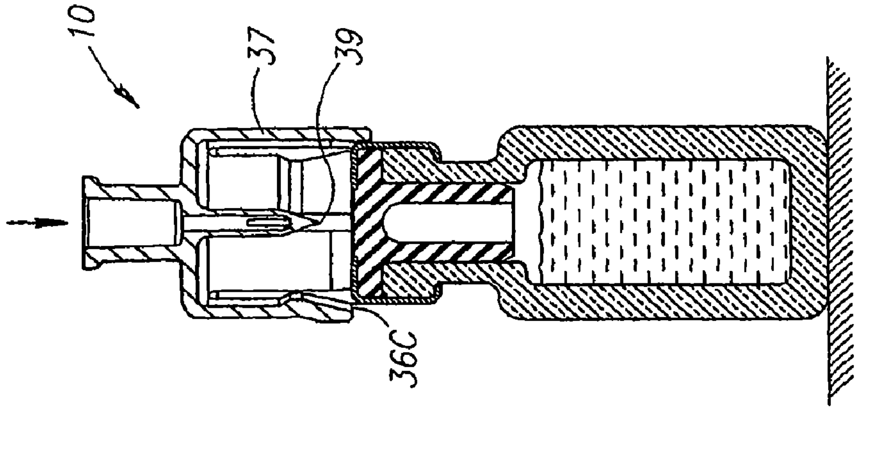
FIG. 3D is a longitudinal cross section of the liquid drug transfer device slightly depressed toward the medicinal vial.

FIGS. 1 and 2 show a liquid drug transfer device 10 for failsafe correct snap fitting on a conventional medicinal vial 11. The vial 11 has a longitudinal axis 12, a bottle portion 13 containing a liquid drug 14, a vial opening 16, an upper peripheral shoulder 15 and a narrow neck 17 intermediate the upper peripheral shoulder 15 of the bottle portion 13 and the vial opening 16. The vial opening 16 is stopped by a typically rubber stopper 18. The stopper 18 has a circular head 19 and a downward depending tubular section 21 with a blind bore 22 having a cross section area A1 in a transverse direction to the longitudinal axis 12. The vial 11 is hermetically sealed by an aluminum band 23 with a rim 24 having an external diameter D1, and an axially directed peripheral surface 26, and exposing a raised central area 27 of the stopper 18. The stopper's central area 27 has a cross section area A2 in a transverse direction to the longitudinal axis 12 where A2>A1. The design feature A2>A1 contributes to misalignment of a vial adapter with respect to a vial for flow communication purposes because users are under the mistaken impression that they have a larger target area for puncturing purposes than they have in practice.

The liquid drug transfer device 10 includes a plastic molded vial adapter 30 having a longitudinal axis 31, and an upright female Luer connector 32 for receiving a syringe (not shown) and integrally formed with the vial adapter 30. The vial adapter 30 includes a top wall 33 transverse to the longitudinal axis 31, and a substantially cylindrical skirt 34 for telescopically slidingly receiving the vial opening 16 therein. The skirt 34 includes three non-adjacent axially directed vial retention flex members 36 and three non-adjacent axially directed vial guidance flex members 37 resiliently elastically attached to the top wall 33. The guidance flex members 36, 37 form an exterior wall of the vial adapter 30. The vial adapter 30 includes an integrally formed hollow puncturing spike 38 in flow communication with the female Luer connector 32. The puncturing spike 38 has a tip 39 with a flow aperture 41 theretowards.

The vial retention flex members 36 have inside surfaces 36A and outwardly taper to flex member tips 36B with an internal diameter D2>D1 and having a length L1 relative to the top wall 33. The inward surfaces 36A are provided with circumferentially extending inwardly protruding vial retention ribs 36C for snap fitting over the vial opening 16 for vial retention purposes. The puncturing spike's tip 39 downwardly extends slightly past the vial retention ribs 36C such that the puncturing spike's flow aperture 41 resides in a vial's blind bore 22 on snap fitting the liquid rug transfer device 10 on a vial 11. The vial guidance flex members 37 have straight inside surfaces 37A and extend to flex member tips 37B with an internal diameter D3 where D2>D3>D1 and having a length L2>L1 relative to the top wall 33. The flex member tips 37B downwardly extend beyond the flex member tips 36B such that the former contact a band's rim 24 before the puncturing spike's tip 39 contacts the vial's stopper 18 for positively guiding the liquid drug delivery device 10 in concentric alignment with the vial 11.

The failsafe correct snap fitting of a liquid drug delivery device 10 on a vial 11 is now described with reference to FIGS. 3A to 3E: Users are prone to inaccurately align a liquid drug delivery device 10 with respect to a vial 11 either by off centering the liquid drug delivery device 10 (see FIG. 3A) or approaching the vial 11 at an angle (see FIG. 3B). The vial guidance flex members 37 assist a user to co-axially align the liquid drug delivery device 10 relative to the vial 11 such that its flex member tips 37B simultaneously contact the band's rim 24 before its puncturing spike's tip 39 contacts the vial's stopper 18 (see FIG. 3C). Initial depression of the liquid drug delivery device 10 towards the vial 11 causes the vial guidance flex members 37 to flex slightly outward as they travel along the aluminum band's peripheral surface 26 and the puncturing spike's tip 39 to approach the vial's stopper 18 before contacting same at about the same time that the inside surfaces 36B under the vial retention ribs 36C touch the band's rim 24 (see FIG. 3D). Continued depression of the liquid drug delivery device 10 towards the vial 11 causes the vial guidance flex members 37 to slide over the band's peripheral surface 19 and the vial retention flex members 36 to snap fit over the vial opening 16 and the flow aperture 41 to be positioned midway along the stopper's blind bore 22 for effecting flow communication with the female Luer connector 32 (see FIG. 3E). The vial guidance flex members 37 have a length and sufficient flexibility to extend radially outwardly beyond the upper peripheral shoulder 15 of the bottle portion 13 of the vial 11, such that the inside surface 37A of each vial guidance flex member 37 rests against the upper peripheral shoulder 15 and the tip 37B of each vial guidance flex member 37 extends radially outwardly beyond the upper peripheral shoulder 15 and radially outwardly beyond a periphery 33*a* of the top wall 33 of the vial adapter 30.

Figure 4:
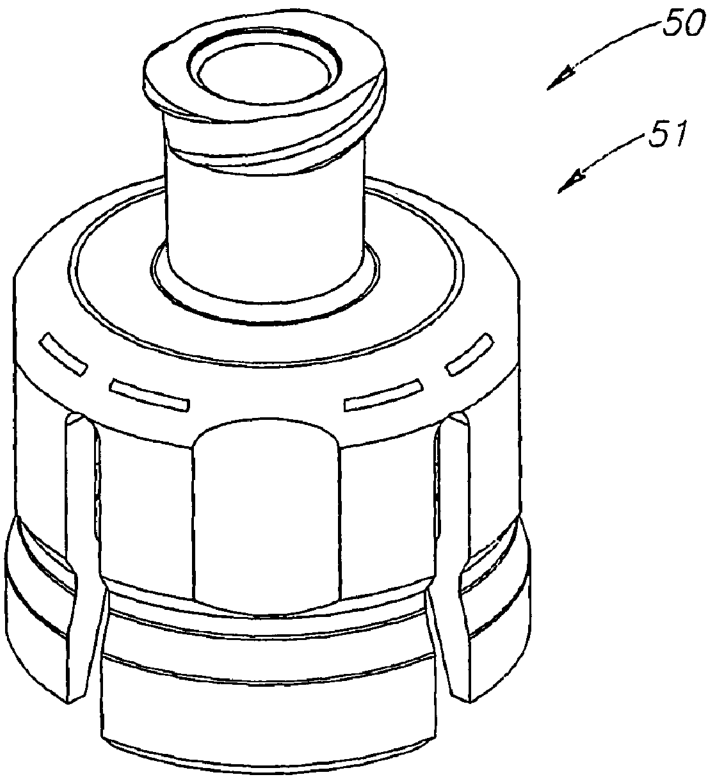
FIG. 4 is a pictorial view of a second preferred embodiment of a liquid drug transfer device with a vented vial adapter for failsafe correct snap fitting on a medicinal vial.

FIG. 4 shows a liquid drug transfer device similar 50 in construction and use as the liquid drug transfer device 10 and differing therefrom insofar that the former is vented and includes a vial adapter 51 with two non-adjacent axially directed vial retention flex members 36 and two non-adjacent axially directed vial guidance flex members 37.

Figure 5:
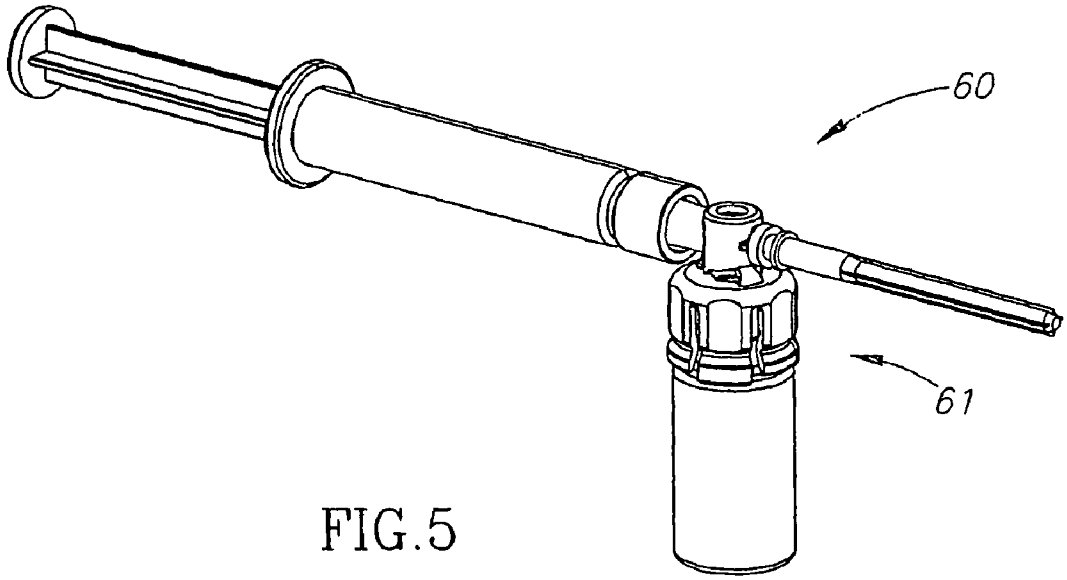
FIG. 5 is a pictorial view of a MIXJECT® fluid control device with a vial adapter for failsafe correct snap fitting on a medicinal vial.

FIG. 5 shows a MIXJECT® fluid control device 60 with a detachable vial adapter 61 similar to the vial adapter 30 for failsafe correct snap fitting on a medicinal vial.

While the invention has been described with respect to a limited number of embodiments, it will be appreciated that many variations, modifications, and other applications of the invention can be made within the scope of the appended claims.

The invention claimed is:

1. Liquid drug transfer device for failsafe correct snap fitting on a medicinal vial having a longitudinal axis and including a bottle portion having an upper peripheral shoulder containing a medicament, a vial opening with a rim and an axially directed peripheral surface and stopped by a stopper, and a narrow neck intermediate the upper shoulder of the bottle portion and the vial opening, the liquid drug transfer device comprising:

(a) a vial adapter having a longitudinal axis, and including a top wall transverse to said longitudinal axis, a substantially cylindrical skirt of at least four axially directed flex members resiliently elastically attached to said top wall and downwardly depending therefrom for telescopically slidingly receiving the vial opening therein, and a hollow puncturing spike for puncturing the stopper, said puncturing spike having a tip with at least one flow aperture for accessing the vial's interior, said at least four flex members including at least two non-adjacent vial retention flex members with at least partially circumferentially extending inwardly protruding vial retention ribs a first distance from said top wall for snap fitting over the vial opening for vial retention purposes, and at least two non-adjacent vial guidance flex members longer than said at least two non-adjacent vial retention flex members relative to said top wall for simultaneously contacting the vial opening's rim for aligning said vial adapter with the vial prior to said snap fitting; and (b) at least one access port in flow communication with said puncturing spike, characterized in that said at least four flex members form an exterior wall of the vial adapter, and said two non-adjacent vial guidance flex members have a generally smooth internal surface at said first distance from said top wall and a length and sufficient flexibility to extend radially outwardly beyond the upper peripheral shoulder of the bottle portion of the vial, such that an internal surface of the vial guidance flex members rests against the upper peripheral shoulder and a terminal portion of the vial guidance flex members extends radially outwardly beyond the upper peripheral shoulder and radially outwardly beyond a periphery of the top wall of the vial adapter such that said at least two non-adjacent vial guidance flex members are employed for vial alignment purposes.

2. The device according to claim 1 wherein said skirt includes three non-adjacent vial retention flex members and three non-adjacent vial guidance flex members.

* * * * *